US010190159B2

(12) United States Patent
Astier

(10) Patent No.: US 10,190,159 B2
(45) Date of Patent: Jan. 29, 2019

(54) METHODS AND SYSTEMS FOR NUCLEIC ACID SEQUENCING BY TUNNELING RECOGNITION

(71) Applicant: Roche Sequencing Solutions, Inc., Pleasanton, CA (US)

(72) Inventor: Yann Astier, Livermore, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 72 days.

(21) Appl. No.: 15/610,186

(22) Filed: May 31, 2017

(65) Prior Publication Data

US 2017/0342480 A1 Nov. 30, 2017

Related U.S. Application Data

(60) Provisional application No. 62/343,715, filed on May 31, 2016.

(51) Int. Cl.
*C12Q 1/6869* (2018.01)
*G01N 33/487* (2006.01)
*G01N 27/327* (2006.01)

(52) U.S. Cl.
CPC ....... *C12Q 1/6869* (2013.01); *G01N 27/3278* (2013.01); *G01N 33/48721* (2013.01)

(58) Field of Classification Search
CPC ........... C12Q 1/6869; G01N 33/48721; G01N 27/3278
See application file for complete search history.

(56) References Cited

U.S. PATENT DOCUMENTS

| 7,238,485 B2 | 7/2007 | Akeson et al. |
| 2014/0008225 A1 | 1/2014 | Jeon et al. |
| 2015/0344945 A1 | 12/2015 | Mandell et al. |

(Continued)

FOREIGN PATENT DOCUMENTS

DE 2013-214341 A1 1/2015

OTHER PUBLICATIONS

International Search Report and Written Opinion from PCT Appln. PCT/EP2017/063125 dated Aug. 1, 2017; 6 pages.
(Continued)

*Primary Examiner* — J. Christopher Ball
(74) *Attorney, Agent, or Firm* — Kilpatrick Townsend and Stockton LLP

(57) ABSTRACT

Embodiments may include a method of analyzing a nucleic acid molecule. The method may include attaching the nucleic acid molecule to a protein. The protein may be attached to a particle with a first diameter. The method may also include applying an electric field to move a first portion of the nucleic acid molecule into an aperture. The aperture may be defined by a first electrode, an insulator, and a second electrode. The aperture may have a second diameter less than the first diameter. The method may further include contacting the first portion of the nucleic acid molecule to both the first electrode and the second electrode. The method may include applying a voltage across the first electrode and the second electrode. The current through the electrodes and the portion of the nucleic acid molecule may be measured, and a nucleotide of the nucleic acid molecule may be identified.

30 Claims, 9 Drawing Sheets

(56) References Cited

U.S. PATENT DOCUMENTS

2016/0258939 A1* 9/2016 Morin .............. G01N 33/54366
2017/0159115 A1* 6/2017 Kokoris ............... C12Q 1/6869

OTHER PUBLICATIONS

Zhao, Y. et al.; "Single-molecule spectroscopy of amino acids and peptides by recognition tunnelling"; *Nature Nanotechnology*; vol. 9, No. 6; Apr. 6, 2014; pp. 466-473.

Zakeri, B. et al.; "Peptide tag forming a rapid covalent bond to a protein, through engineering a bacterial adhesin"; *Proc. Natl. Acad. Sci.*, vol. 109, No. 12; Mar. 20, 2012; pp. E690-E697.

Zhao et al.; "Single-molecule spectroscopy of amino acids and peptides by recognition tunneling"; *Nature Nanotech.*; vol. 9, No. 6; Jun. 2014; pp. 466-473.

* cited by examiner

METHODS AND SYSTEMS FOR NUCLEIC ACID SEQUENCING BY TUNNELING RECOGNITION

CROSS-REFERENCES TO RELATED APPLICATIONS

This application claims priority to U.S. Provisional Application No. 62/343,715, filed May 31, 2016, which is incorporated herein by reference in its entirety for all purposes.

BACKGROUND

Nanopore-containing devices have been targeted for the development of new analytical methods. Nanopores may have the ability to detect single molecules, which may be promising technology in the field of chemical and biological detection. For example, nanopores may be used for diagnostics and nucleic acid sequencing. Solid state nanopore bio-sensing may be a rapid single molecule sensing technique. In some cases, solid state nanopores form a channel in an ionic liquid between two electrodes. The two electrodes may not be part of the nanopore itself but may be positioned in the ionic liquid. As a molecule passes though the nanopore channel, the current and other electrical characteristics through the channel change. These electrical characteristics can provide information on the molecule, but fabrication issues may make identifying individual nucleotides in a nucleic acid molecule difficult. Multiple nucleotides may be present in the aperture at the same time or may pass through the aperture quickly, which may not provide a strong enough signal for differentiating nucleotides.

Nanopore devices may be used with tunneling recognition. Tunneling recognition is based on placing a chemical entity between electrodes, which may be in the nanopore device itself. The orbitals of the chemical entity will allow electrons to transfer from one electrode to the other, creating a tunneling current. Dimensions and other properties of solid state nanopores may be difficult to adapt to a mass production process. To sequence nucleic acid molecules with ionic current, nanopore dimensions may need to be on the order of nanometers, which may be less than 2 nm. Creating a channel of this size may require precise and expensive techniques. However, reducing dimensions of the nanopore may result in incomplete or poor wetting needed for the nanopore to function as a sensing device. Improvements in the design and manufacturability of nanopore-containing devices used in chemical and biological detection and processes involving the devices are still needed. Design and manufacturability improvements should not come at the expense of accurate and precise analysis. These and other issues are addressed by the technology described in this document.

BRIEF SUMMARY

Embodiments of the present technology may allow for the sequencing of nucleic acid molecules by tunneling recognition. A nucleic acid molecule may be driven into a channel by an electric field or a pressure gradient. In the channel, a portion of the nucleic acid molecule may enter a gap between two electrodes. Electrodes with a small gap between them may allow for tunneling recognition, but nucleic acid molecules may not diffuse frequently enough into small gaps to obtain an adequate tunneling signal. The electric field or pressure gradient may drive nucleic acid molecules into the electrode gap more easily and frequently. Small gaps, which may be 1-2 nm wide, may be difficult or expensive to manufacture. In some instances, the gap may be between two electrodes aligned parallel to each other but not in the same plane, which may be easier to manufacture than a gap between the ends of two coplanar electrodes. The nucleic acid molecule may be tethered to a motor protein, which may be attached to a particle or a bead. The particle may be larger than the channel. The particle may anchor one end of the nucleic acid molecule while an electric field or a flow pulls the nucleic acid molecule through the channel. In this manner, the nucleic acid molecule may be stretched along the channel, and may oscillate in the channel as a result of Brownian motion. The nucleic acid molecule may stochastically interact with the tunneling electrodes to yield a tunneling signal.

A voltage may be applied to the electrodes. When a portion of the nucleic acid molecule is within the gap between the electrodes and the nucleic acid molecule bridges two electrodes, electrons may tunnel through the nucleic acid molecule from one electrode to the other, generating a current. The current may be measured. The nucleic acid molecule may oscillate in the gap, and the measured current may have an amplitude and frequency. The amplitude and frequency may be variable. The characteristics of the current may aid in identifying a particular nucleotide or base present in the nucleic acid molecule. The electrical characteristics may serve almost as a fingerprint in identifying a nucleotide of the nucleic acid molecule. The motor protein may feed through or pull in the nucleic acid molecule so that a different nucleotide is in the electrode gap and a different current signal can be measured. As a result, an additional nucleotide can be identified. More nucleotides can be moved into the electrode gap so multiple nucleotides of the nucleic acid may be identified and the nucleic acid may be sequenced.

Embodiments may include a method of analyzing a nucleic acid molecule. The method may include attaching a nucleic acid molecule to a protein. The protein may be attached to a particle with a first diameter. The method may also include applying an electric field to move a first portion of the nucleic acid molecule into an aperture. The aperture may be defined by a first electrode, a first insulator, and a second electrode. The aperture may have a second diameter less than the first diameter. The method may further include contacting the first portion of the nucleic acid molecule to both the first electrode and the second electrode. In addition, the method may include applying a voltage across the first electrode and the second electrode. The current through the first electrode, the nucleic acid molecule, and the second electrode may be measured. Based on the current, a nucleotide of the nucleic acid molecule may be identified.

Some embodiments may include a nucleic acid molecule analysis system. The system may include a nucleic acid molecule attached to a protein. The protein may be attached to a particle with a diameter. The system may also include an aperture defined by a first electrode, a first insulator, and a second electrode. The aperture may have a diameter less than the diameter of the particle. The system may further include a first power supply in electrical communication with the first electrode and the second electrode. In addition, the system may include a second power supply configured to apply an electric field through the aperture.

Additional embodiments may include a method of analyzing a nucleic acid molecule. The method may include attaching a nucleic acid molecule to a protein. The protein may be attached to a particle with a first diameter. The method may also include moving a first portion of the nucleic acid molecule into an aperture defined by an insulator. The aperture may have a second diameter less than the first diameter. The method may further include moving a second portion of the nucleic acid molecule into a gap between a first electrode and a second electrode. The gap may include a line representing the shortest distance between the electrodes. In addition, the method may include contacting the nucleic acid molecule to both the first electrode and the second electrode. In addition, a current through the first electrode, the nucleic acid molecule, and the second electrode may be measured. Based on the current, a nucleotide of the nucleic acid molecule may be identified.

Embodiments may include a nucleic acid analysis system. The system may include a nucleic acid molecule attached to a protein. The protein may be attached to a particle with a first diameter. The system may also include an aperture defined by a first insulator. The aperture may have a second diameter less than the first diameter. The aperture may have a longitudinal axis perpendicular to the diameter. The system may further include a first electrode. A portion of the first electrode may extend into the aperture. The system may also include a second electrode, with a portion of the second electrode extending into the aperture. A plane that includes the portion of the first electrode and the portion of the second electrode may be orthogonal to the longitudinal axis. In addition, the system may include a first power supply in electrical communication with the first electrode and the second electrode.

DEFINITIONS

Figure 1A:
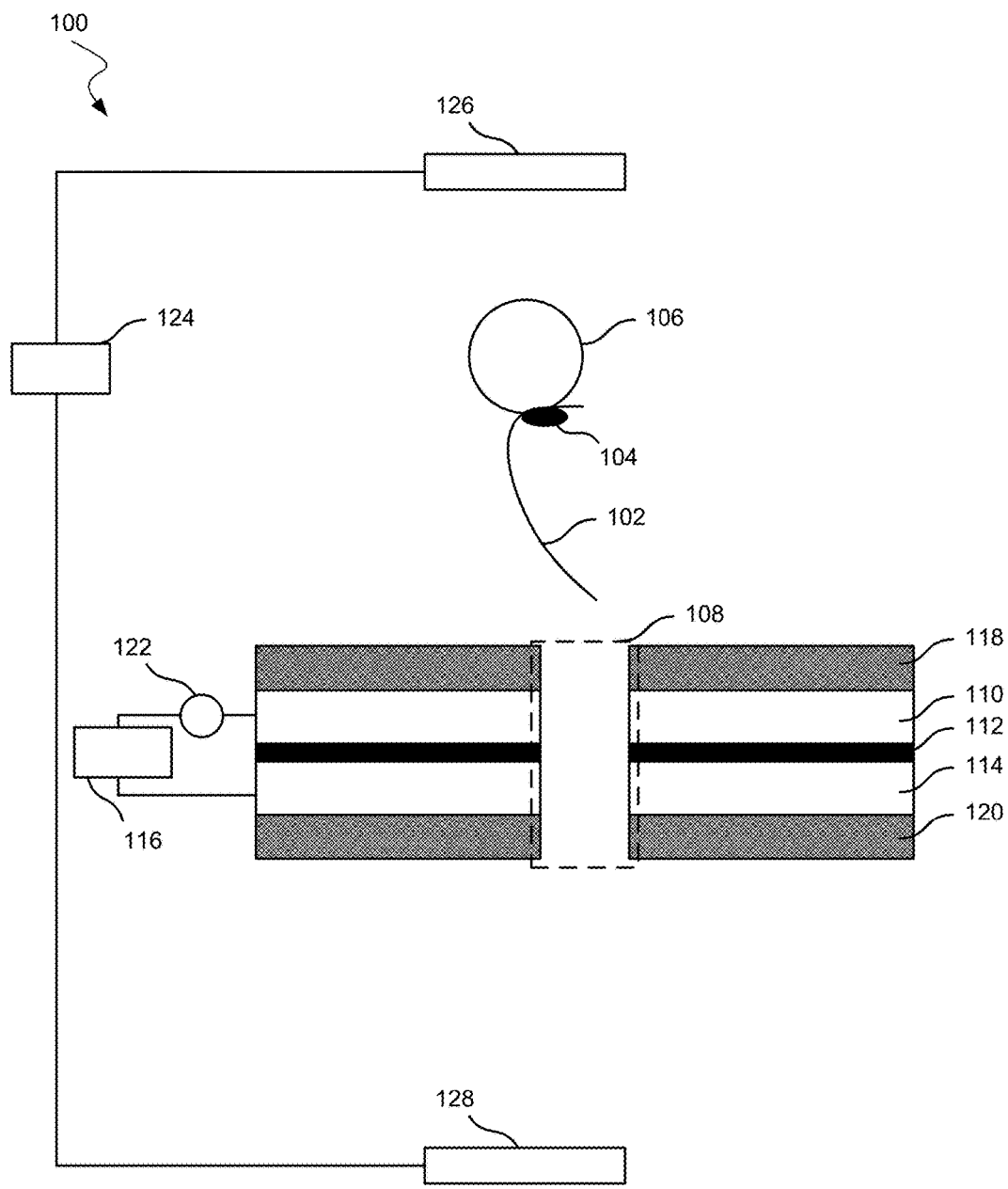
FIG. 1A shows a side view of a nucleic acid molecule analysis system 100 according to embodiments of the present invention.

The term "contacting" may refer to bringing one object in proximity to another object such that electrons may tunnel from one object through the other object. At a subatomic level, two objects may never physically touch each other as repulsive forces from electron clouds in the objects may prevent the objects from coming into closer proximity.

The term "motor protein" may be a molecule that may move a nucleic acid molecule relative to the molecule. For example, the motor protein may remain stationary and the nucleic acid molecule may move, or the nucleic acid molecule may remain stationary and the motor protein may move. A motor protein may include polymerases, helicases, ribosomes, exonucleases, along with other enzymes.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "oscillate" may refer to the motion of an object in a fluid as a result of Brownian motion or other forces. An object may oscillate without active intervention by a person or a machine. In some cases, an object may oscillate as a result of an applied electric field or a pressure-driven flow.

The term "weak force" may refer to one of the fundamental forces in physics.

DETAILED DESCRIPTION

Conventional nanopore-based devices currently on the market may contain protein nanopores inserted in metastable lipid bilayers. The lipid bilayers may be fragile and may undermine the stability of the devices. Solid-state atomic scale nanopore layers may be less fragile than protein nanopores and have the potential for improved manufacturability. Possible methods involving these devices include confining nucleic acid molecules in a gap of 2 nm or less between electrodes and recognizing nucleotides and nucleotide sequences using electrons that tunnel through the electrodes and the nucleic acid molecule. Solid-state nanopores near this dimension may be formed by focusing a beam of electrons or ions on a thin material. This method is difficult to adapt to mass production of nanopores, nanopore-containing devices, and analytical instruments. Additionally, a nucleic acid molecule may be difficult to force into such a small gap between electrodes. Wider channels may allow for a nucleic acid molecule to more easily diffuse into a nanopore channel. However, the nucleic acid molecule may pass through a wider channel too quickly or without the nucleic acid molecule contacting tunneling electrodes. As a result, little or no tunneling current may be measured, and the nucleic acid molecule may not be easily sequenced by the device.

Tunneling recognition may be done in geometries that do not necessarily include nanopores. For example, tunneling electrons may be used in scanning tunneling microscopy (STM), which has been used to image individual atoms. In theory, STM may be used as well to read a DNA sequence, but STM may rely on a mobile electrode probe, and moving the probe electrode may move a DNA sample, making obtaining a quality tunneling signal difficult. Fixing the DNA sample and preventing the DNA from moving may improve tunneling recognition.

Devices and methods described herein may allow for a nucleic acid molecule to be sequenced without forcing the nucleic acid molecule into a nanopore channel with a diameter of 2 nm or less. Instead, a nanopore channel may be 10 nm or more in diameter. A nucleic acid molecule may enter the nanopore channel more easily. Electrode gaps may be 2 nm or less, while the nanopore channel may be a large diameter. For example, electrodes may be stacked on top of each other as layers with a resistive layer in between the two electrodes. The resistive layer may have a thickness on the order of 2 nm. The electrodes and the resistive layer may be exposed in a nanopore channel, with the distance between the electrodes not dependent upon the diameter of the nanopore channel. In some other embodiments, a nanowire may reside in a nanopore channel with a diameter of 10 nm or more. The nanowire may be separated to form a gap of 2 nm or less, and the two separate parts of the nanowire may serve as electrodes. In this manner, the gap between electrodes may not be dependent upon the diameter of the nanopore channel.

In some embodiments, a nucleic acid molecule may be attached to at least one of a bead and a molecular motor protein. The bead may in at least one dimension be larger than a dimension of the nanopore channel so that the bead may not easily or quickly pass through the nanopore channel. The bead may anchor one end of the nucleic acid molecule in the nanopore channel, which may allow the nucleic acid molecule to oscillate and randomly contact electrodes to yield a tunneling signal. The nucleic acid molecule may be driven by an electric field or a pressure-driven flow, and the bead may reduce the possibility of the nucleic acid molecule bunching up. The molecular motor protein may feed in (or pull out) the nucleic acid molecule to the channel, allow for additional portions of the nucleic acid molecule to yield a tunneling signal and therefore be sequenced.

In some embodiments, nanopore devices and methods may allow for a biological polymer molecule, not just nucleic acid molecules, to be analyzed. For example, a protein may be analyzed to determine the amino acids in the protein. The nanopore lengths and diameters may be adjusted for the size of an amino acid instead of the size of a nucleic acid molecule. For example, the distance between electrodes may be on the order of 1-2 nm. In some examples, the distance between electrodes may be from 0.9 to 2.5 nm. Nanopore devices and methods of tunneling recognition are discussed further below.

I. Electrode Stack Tunneling Recognition

Tunneling recognition may be carried out in an electrode stack or sandwich. Two electrodes may be in layers and sandwich an insulator. The distance between the electrodes, which may also be the thickness of the insulator, may be on the order of the size of a nucleotide within a nucleic acid, or about 2 nm. The distance between the electrodes may be independent of any aperture diameter, which may allow for easier manufacturability. Embodiments described herein may also be modified to analyze biological polymer molecules other than nucleic acid molecules, including proteins.

A. System

Figure 1B:
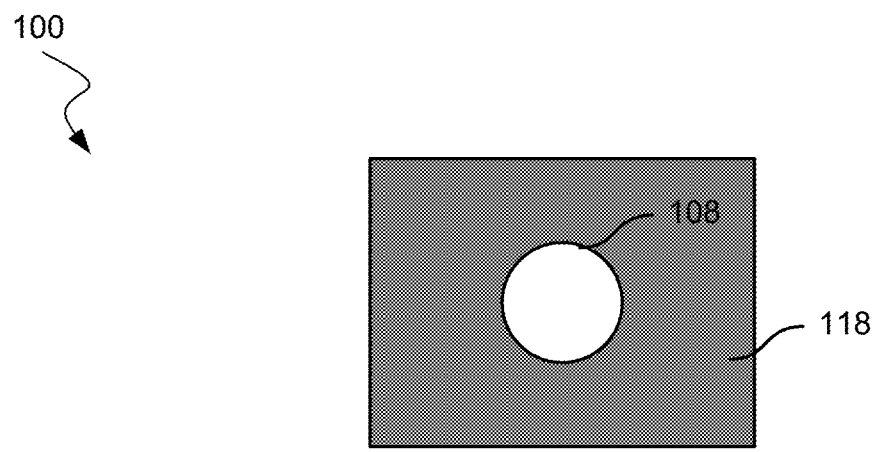
FIG. 1B shows a top view of a nucleic acid molecule analysis system 100 according to embodiments of the present invention.

As shown in FIG. 1A and FIG. 1B, some embodiments may include a nucleic acid molecule analysis system 100. FIG. 1A shows a side view of system 100, and FIG. 1B shows a top view of system 100. "Side" and "top" are used to describe system 100 in the figures, but system 100 may be rotated so that any part of system 100 may point in any direction. System 100 may include a protein 104 attached to a particle 106 having a diameter. If particle 106 is not spherical, particle 106 may have a characteristic dimension. Particle 106 may have a diameter or characteristic dimension in a range from 10 nm to 15 nm, 15 nm to 20 nm, 20 nm to 30 nm, 30 nm to 40 nm, 40 nm to 50 nm, or 50 nm or more in embodiments. The particle may be a bead. Protein 104 may be a molecular motor protein. A molecular motor protein may include polymerases, helicases, ribosomes, and exonucleases.

Protein 104 may be covalently attached to particle 106. For example, the surface of particle 106 may be modified with Streptavidin, and protein 104 may be modified with biotin. In some embodiments, the surface of particle 106 may be modified with biotin, and protein 104 may be modified with biotin. Streptavidin can bind to biotin, which may then bind protein 104 to particle 106. Similarly, in other examples, the surface of particle 106 may be modified with SpyTag peptide, and protein 104 may be modified with SpyCatcher protein. Alternatively, the surface of particle 106 may be modified with SpyCatcher, and protein 104 may be modified with SpyTag. Covalent bonding between SpyTag and SpyCatcher may bind protein 104 to particle 106. (See B. Zakeri et al., "Peptide tag forming a rapid covalent bond to a protein, through engineering a bacterial adhesin," *Proc. Natl. Acad. Sci.*, 109 (2012), pp. E690-97, the contents of which are incorporated herein by reference for all purposes.)

A nucleic acid molecule 102 may be introduced to the system with protein 104 attached to particle 106. Nucleic acid molecule 102 may include single-stranded DNA or RNA. Nucleic acid molecule 102 may attach to protein 104.

System 100 may also include an aperture 108 defined by a first electrode 110, a first insulator 112, and a second electrode 114. First electrode and second electrode may include palladium, platinum, gold, or another noble metal.

At least one of the first electrode and the second electrode may be coated with an adapter molecule. The adapter molecule may undergo weak force chemical interactions with the nucleic acid molecule. As a result, the adapter molecule may aid the nucleic acid molecule in bridging or contacting the two electrodes. An adapter molecule may be organic or organometallic.

First insulator 112 may include a photoresist. The thickness of first insulator 112 (i.e., the distance separating first electrode 110 and second electrode 114) may be 1 nm or less, 2 nm or less, 3 nm or less, 4 nm or less, or 5 nm or less in embodiments. The distance between electrodes may be from 0.9 nm to 2.5 nm, including from 0.9 nm to 1.0 nm, 1.0 nm to 1.5 nm, 1.5 nm to 2.0 nm, or 2.0 nm to 2.5 nm. Aperture 108 may be defined by a sidewall. The sidewall may include a second insulator 118, first electrode 110, first insulator 112, second electrode 114, and third insulator 120. Second insulator 118 and third insulator 120 may include a photoresist, glass, and/or silicon nitride. As shown in FIG. 1A, first electrode 110 may be between second insulator 118 and first insulator 112. Second electrode 114 may be between first insulator 112 and third insulator 120. System 100 may include a sandwich of layers in the following order: second insulator 118, first electrode 110, first insulator 112, second electrode 114, and third insulator 120. The layers in the sandwich may be in contact with a neighboring layer or neighboring layers.

Aperture 108 may have a diameter less than the diameter of particle 106. If aperture 108 is not circular or cylindrical, aperture 108 may have a characteristic dimension less than the characteristic dimension of particle 106. The aperture may include a beveled opening or include geometries similar to a cone. If particle 106 is not circular, particle 106 may be described by a characteristic dimension. The characteristic dimension may describe a length, a width, a length of a major axis, or a length of a minor axis. The characteristic dimension may be equal to the calculated diameter of a sphere having a volume equal to the particle. The diameter or the characteristic dimension of the aperture may be in a range from 10 nm to 15 nm, 15 nm to 20 nm, 20 nm to 30 nm, 30 nm to 40 nm, or 40 nm to 50 nm in embodiments. The diameter or the characteristic dimension of aperture 108 may be more than 1 nm, more than 5 nm, or more than 10 nm shorter than the diameter or characteristic dimension of particle 106. The diameter or characteristic dimension of particle 106 may be a value that is large enough to prevent particle 106 from traversing too quickly through aperture 108 with a diameter or characteristic dimension.

System 100 may further include a first power supply 116 in electrical communication with first electrode 110 and second electrode 114. First power supply 116 may apply a voltage to first electrode 110 and second electrode 114. First power supply 116 may be configured to maintain a desired current or a desired voltage. The current passing through both electrodes may be measured by a meter device 122. The current passing through both electrodes may include current that tunnels through nucleic acid molecule 102. Meter device 122 may include a current meter, an oscilloscope, or other current-measuring meters. In addition, system 100 may include a second power supply 124 configured to apply an electric field through aperture 108. This electric field may drive nucleic acid molecule 102 through aperture 108. A liquid may be disposed in aperture 108. The liquid may be an electrically conductive solution and allow nucleic acid molecule 102 to flow through aperture 108. Second power supply 124 may be in electrical communication with a third electrode 126 and a fourth electrode 128. Third electrode 126 and fourth electrode 128 may be disposed in a liquid and disposed on opposite ends of aperture 108.

System 100 may be one of a plurality of analysis systems, allowing for the analysis of thousands to millions of nucleic acid molecules. A plurality of analysis systems may share the same second power supply used to drive nucleic acid molecules through the aperture. In the case of a plurality of analysis systems, the diameters and characteristic dimensions may be the mean or median diameter or characteristic dimension of the plurality. Using a plurality of analysis systems may allow multiplexing, which may be an advantage over other tunneling recognition systems.

Systems may also include a biological polymer analysis system, where a biological polymer molecule, instead of a nucleic acid molecule, is analyzed. For example, a system similar to system 100 may be used to analyze a protein and the amino acids of the protein.

B. Method

Figure 2:
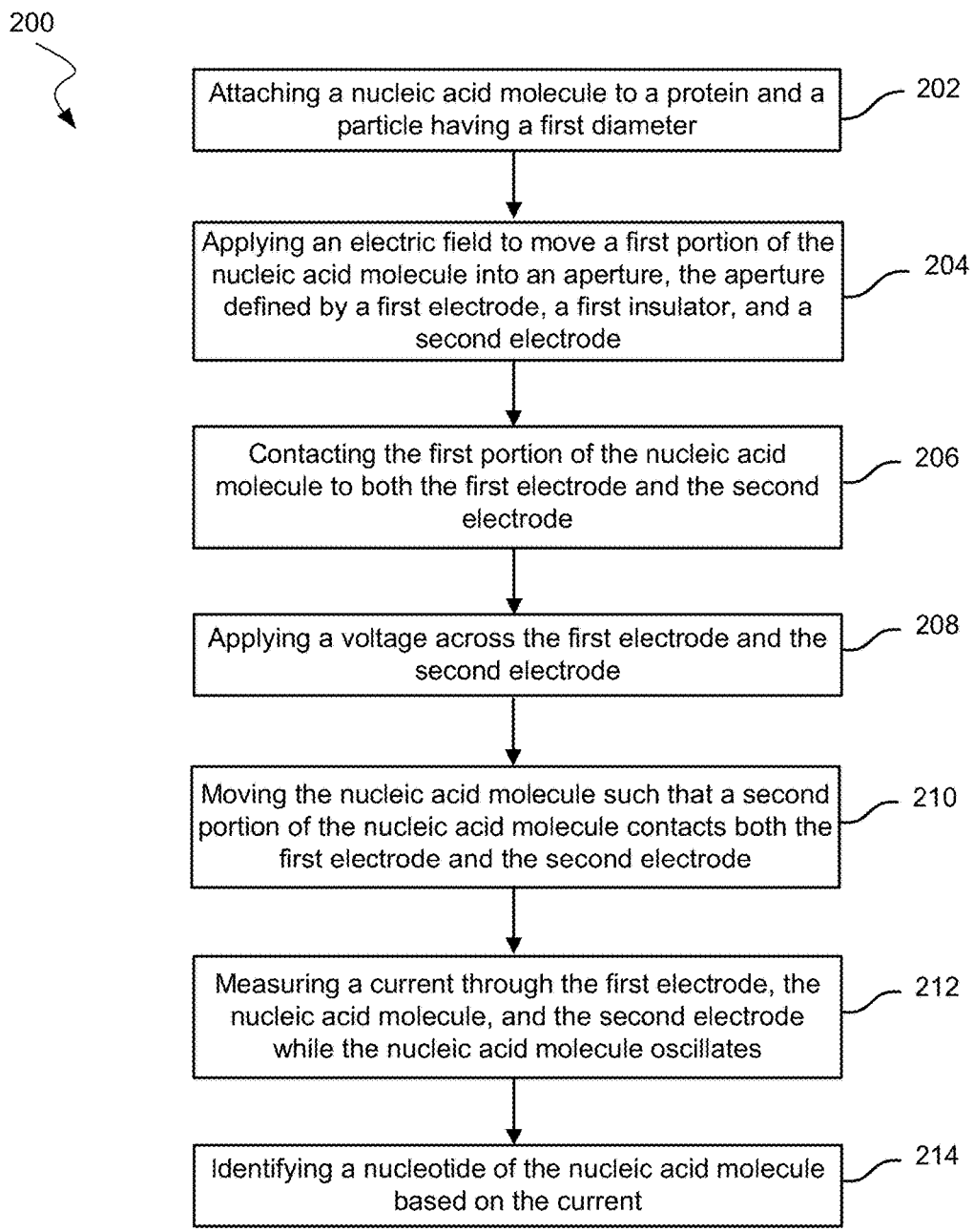
FIG. 2 is a flowchart of a method 200 of analyzing a nucleic acid molecule according to embodiments of the present invention.

As shown in FIG. 2, embodiments may include a method 200 of analyzing a nucleic acid molecule.

At block 202, method 200 may include attaching a nucleic acid molecule to a protein. The protein typically may have a binding site for a nucleic acid, similar to a binding site of an enzyme for a substrate. The protein and nucleic acid may form a non-covalent bond, with a strength depending on the protein or enzyme involved. The protein may be attached to a particle with a first diameter. The nucleic acid molecule, protein, and particle may be any described herein.

At block 204, method 200 may also include applying an electric field to move a first portion of the nucleic acid molecule into an aperture. The first portion of the nucleic acid molecule may include a nucleotide. The aperture may be defined by a first electrode, a first insulator, and a second electrode. The aperture may have a second diameter less than the first diameter. The nucleic acid molecule may be in a fluid, and the electric field may be applied through electrodes in the fluid, where the electrodes may be located on opposite ends of the aperture.

At block 206, method 200 may further include contacting the first portion of the nucleic acid molecule to both the first electrode and the second electrode (block 206).

Figure 3A:
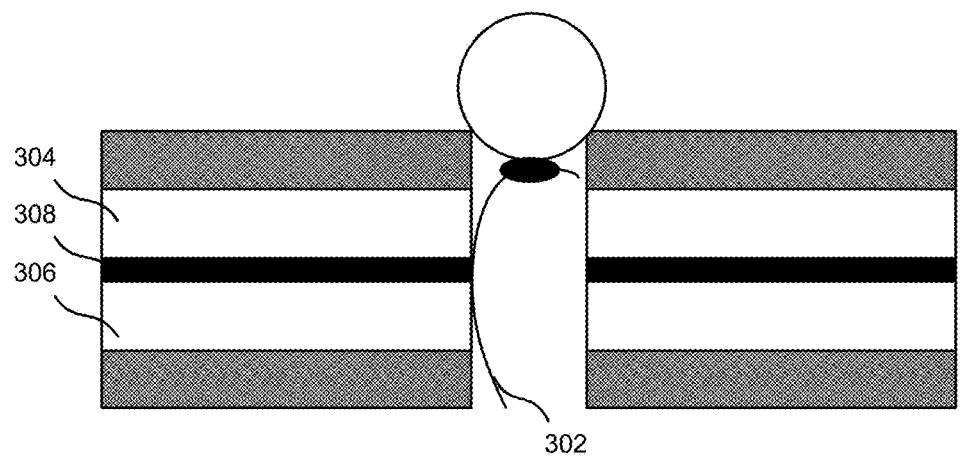
FIG. 3A shows a nucleic acid molecule contacting electrodes to allow for tunneling recognition in a nucleic acid molecule analysis system according to embodiments of the present invention.
Figure 3B:
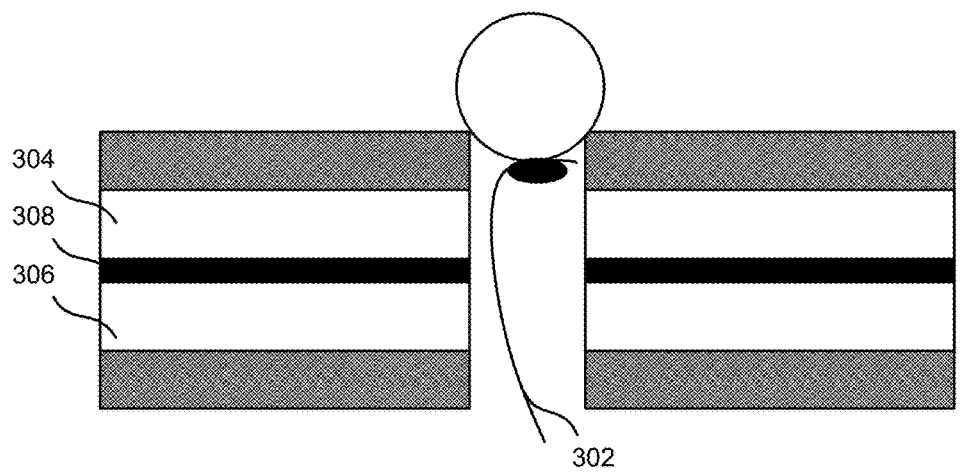
FIG. 3B shows a nucleic acid molecule not contacting electrodes in a nucleic acid molecule analysis system according to embodiments of the present invention.

FIG. 3A shows a portion of nucleic acid molecule 302 contacting first electrode 304 and second electrode 306 across insulator 308. When a portion of nucleic acid molecule 302 contacts both electrodes, the molecule may also be considered to bridge both electrodes. When a portion of nucleic acid molecule 302 contacts both electrodes, electrons may tunnel from one electrode to the other. The current generated by the tunneling electrodes may be measured. As shown in FIG. 3B, if nucleic acid molecule 302 does not contact first electrode 304 or second electrode 306, then electrons may not tunnel through the electrodes and no current may be measured.

At block 208, method 200 may include applying a voltage across the first electrode and the second electrode. The electrodes may be considered tunneling electrodes and may be any electrode described herein. The voltage may be direct current or alternating current voltage. The voltage may be applied in pulses or in a waveform (e.g., sine, square, triangle, or sawtooth). Method 200 may also include applying a current through the first electrode and the second electrode.

At block 210, method 200 may include moving the nucleic acid molecule such that a second portion of the nucleic acid molecule contacts both the first electrode and the second electrode. The second portion of the nucleic acid molecule may be in a different location than the first portion of the nucleic acid molecule. The second portion of the nucleic acid molecule may include a nucleotide. The nucleic acid molecule may be moved using the protein. In some cases, the second portion of the nucleic acid molecule may be positioned closer to the protein than the first portion of the nucleic acid molecule is positioned to the protein. In other cases, the second portion of the nucleic acid molecule may be positioned farther from the protein than the first portion is position from the protein.

Figure 4A:
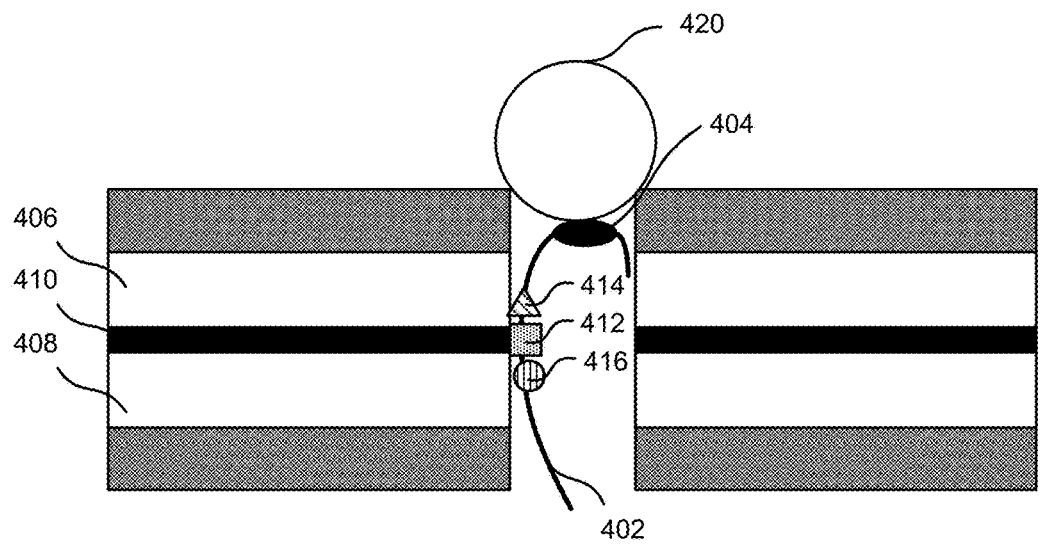
FIG. 4A shows a nucleic acid molecule contacting two electrodes before being moved by a molecular motor protein according to embodiments of the present invention.
Figure 4B:
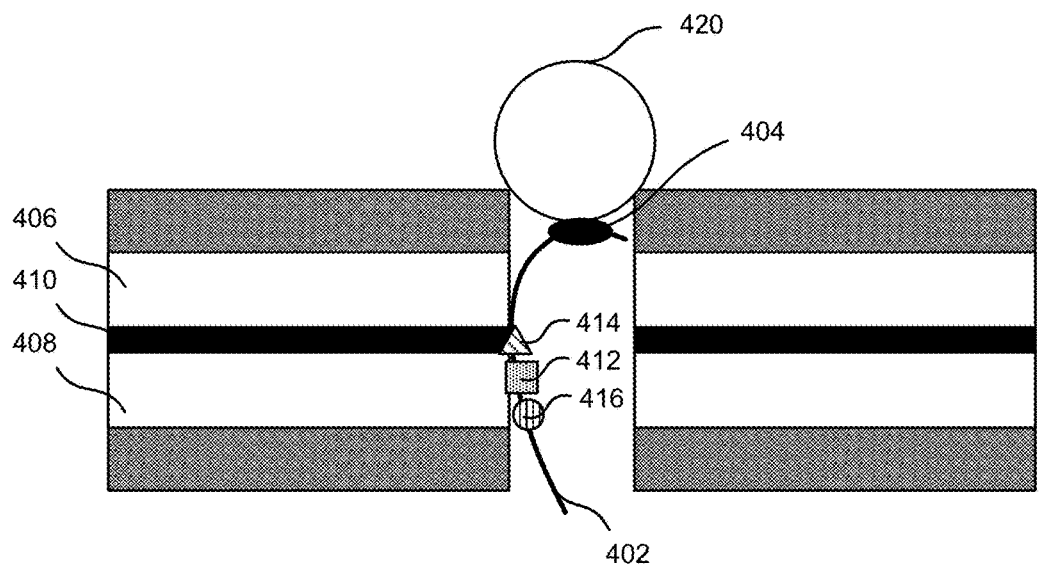
FIG. 4B shows a nucleic acid molecule contacting two electrodes after being moved by a molecular motor protein according to embodiments of the present invention.

FIG. 4A and FIG. 4B show diagrams of how a nucleic acid molecule 402 may be moved by a protein 404. In FIG. 4A, nucleic acid molecule 402 contacts a first electrode 406 and a second electrode 408 across insulator 410. Nucleic acid molecule 402 may contact the electrodes in a way such that electrons tunnel through a nucleotide 412. Nucleotide 412 may be any of the nucleotide bases, including A, C, G, T, and U, and may be a labeled, artificial, or methylated nucleotide. A nucleotide 414 may be closer to protein 404 than nucleotide 412 is to protein 404, while a nucleotide 416 may be farther away. Electrons may not tunnel through either nucleotide 414 or 416 because these nucleotides are not positioned between the electrodes. Protein 404 may move nucleic acid molecule 402 away from or toward a particle 420. FIG. 4B shows an example of nucleic acid molecule 402 from FIG. 4A moving away from particle 420. Protein 404 may move nucleic acid molecule 402 so that nucleotide 412 is no longer aligned so that electrons may tunnel through nucleotide 412. Instead, nucleotide 414 may be aligned so that electrons tunnel through nucleotide 414. Electrons tunneling through a different nucleotide may generate different current characteristics. In some embodiments, electrons may tunnel through two or more nucleotides.

The nucleic acid molecule may oscillate in the aperture. The nucleic acid molecule may oscillate as a result of Brownian motion. In some embodiments, oscillation may be partly or wholly a result of an applied electric field, pressure-driven flow, or a change in an electric field or flow. The oscillation of the nucleic acid molecule may change the portion of the nucleic acid molecule contacting or bridging the electrodes. In some instances, the nucleic acid molecule may oscillate between a configuration similar to FIG. 3A, where a portion of the nucleic acid molecule contacts both electrodes, and a configuration similar to FIG. 3B, where a nucleic acid molecule does not contact both electrodes. In some configurations, a portion of the nucleic acid molecule may still make contact with both electrodes but in a manner that allows the electrons to more easily or less easily tunnel through. For example, the nucleic acid molecule may not make a full contact with one of the electrodes. As a result, the oscillation may affect the current passing through the electrodes and the nucleic acid.

At block 212, the current through the first electrode, the first portion of the nucleic acid molecule, and the second electrode may be measured while the nucleic acid molecule oscillates in the aperture. The oscillating nucleic acid may affect at least one of the amplitude, pulse width, and frequency of the current. The pulse width may also be considered a dwell time, which may be related to the duration of a certain portion of the nucleic acid molecule remaining in contact with both electrodes. In some embodiments, voltage or resistance may be measured instead of or in addition to current. In some embodiments, the electrical characteristic may be transformed by a mathematical operation, such as a Fourier transform, and the transform may be analyzed. In embodiments, the measured electrical characteristic may be compared to the applied voltage and adjusted to isolate the oscillation of the nucleic acid molecule.

At block 214, based on the current, the nucleotide of the first portion of the nucleic acid molecule may be identified. The current may be compared to a calibration current measured from a known nucleotide or a known sequence. Nucleotides or sequences may have a current pattern that serves as a fingerprint to identify the nucleotide or sequence. The amplitude, frequency, and/or pulse width of the measured current may be used to identify the unknown nucleotide or sequence based on a known nucleotide or sequence. The amplitude may depend on the individual nucleotide and the resistance of the nucleotide. The frequency may depend on how the nucleotide and/or neighboring nucleotides oscillate in the aperture. For example, a pattern may be recognized and matched to a known nucleotide or sequence. An exact match may not be needed. Instead, if a current measured from an unknown nucleotide or sequence has a certain threshold level of amplitude, frequency, and/or pulse width, the nucleotide or sequence may be identified. Analyzing the current characteristics may be similar to analyzing electrical characteristics from resonant-tunneling diodes. Tunneling recognition of nucleotides may be similar to tunneling recognition of amino acids as described by Zhao et al., "Single-molecule spectroscopy of amino acids and peptides by recognition tunneling," *Nature Nanotech.* 9, (2014) 466-73, the contents of which are incorporated herein by reference for all purposes.

In embodiments, one or more nucleotides may be labeled. A nucleotide may be labeled with a chemical compound that yields tunneling currents that are stronger than the nucleotide without the chemical compound. The label may be specific to the type of nucleotide it is attached. Labels may include conjugated organic molecules, organometallic compounds, or metal clusters. The labeled nucleotides may be included as labeled nucleotide tri-phosphates in the analysis system.

In some embodiments, the nucleic acid molecule may be circular DNA or a DNA formed with repeated sequences. In embodiments with circular DNA, protein 104 may be a polymerase. The polymerase may copy the circular DNA, and as the polymerase accomplishes a full circle, the single-stranded DNA just synthesized may be moved into the aperture. The "threading" of the aperture by the single-stranded DNA may be controlled by the kinetics of the polymerase and the availability of nucleotide tri-phosphate. As a result of the circular DNA template, the single-stranded DNA may include repeated sequences. The repeated sequences may rotate through the electrodes, which may allow for a better signal to identify nucleotides.

In other embodiments, methods may be used to analyze a biological polymer other than a nucleic acid molecule. For example, the amino acids, rather than the nucleotides, of a protein, rather than a nucleic acid molecule, may be analyzed by methods similar to method 200.

C. Example

Figure 5A:
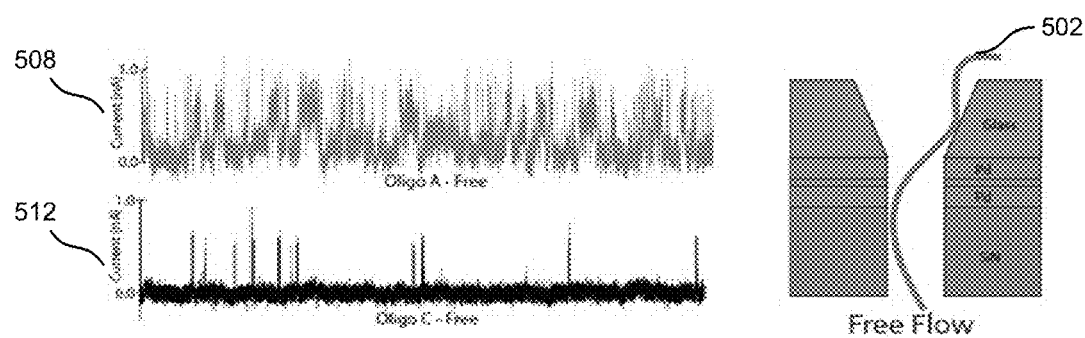
FIG. 5A shows current characteristics of different nucleic acid molecules in free flow according to embodiments of the present invention.
Figure 5B:
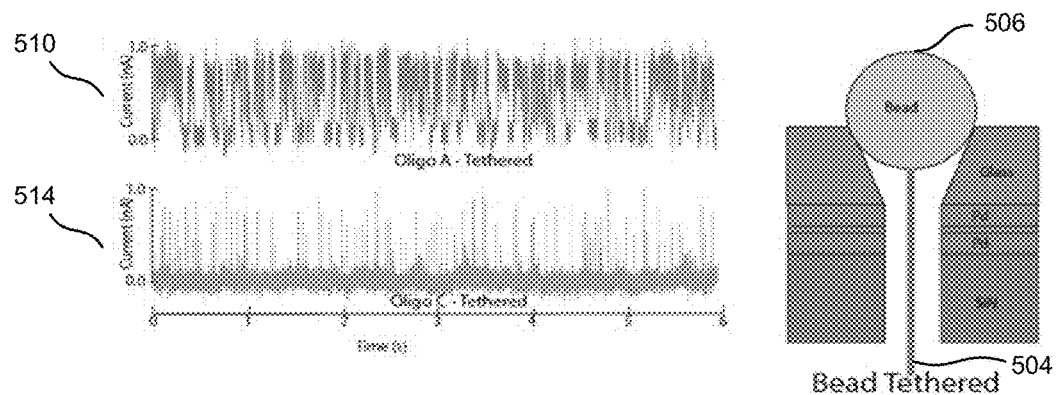
FIG. 5B shows current characteristics of different nucleic acid molecules when tethered to a bead according to embodiments of the present invention.

FIG. 5A and FIG. 5B show how the current characteristics of a nucleic acid molecule 502 that is allowed to flow freely compared with a nucleic acid molecule 504 tethered to a bead 506. Nucleic acid molecule 502 may fit in a channel defined by glass, palladium electrodes, an insulating layer, and silicon nitride, but nucleic acid molecule 502 may flow through the channel too quickly. In some cases, nucleic acid molecule 502 may reside for some time in the channel but may bunch up rather than being a straight or mostly straight strand. Bunching up may mean that the nucleic acid molecule doubles against itself in some areas, which may cause the nucleic acid molecule to not bridge the electrodes. In contrast, nucleic acid molecule 504 tethered to bead 506 may not flow through the channel because bead 506 has a diameter larger than the smallest dimension of the channel opening. In addition, bead 506 may anchor nucleic acid molecule 504 in the channel while an electric field pulls the nucleic acid molecule through the channel. As a result, nucleic acid molecule 504 may be straight or mostly straight and may not bunch up. Even though nucleic acid molecule 504 may not bunch up, Brownian motion may move nucleic acid molecule 504 so that electrons may tunnel through nucleic acid molecule 504.

Both FIG. 5A and FIG. 5B show an aperture with a bevel in the glass insulator. This bevel may be a result of the nano-fabrication process. In many cases, the sidewalls of the aperture may not be completely straight and may be beveled or slanted as would be expected from the control and accuracy of fabrication techniques, including etching. A molecular motor protein was not used with the embodiment in FIG. 5B to simplify the experimental setup.

Graphs 508, 510, 512, and 514 show current measurements resulting from electrons tunneling through nucleic acid molecules. Graph 508 shows current measurements from a nucleic acid molecule, "Oligo A," that is not tethered to a bead, while graph 510 shows current measurements from the same type of nucleic acid molecule but tethered to a bead. Graph 512 shows current measurements from a different nucleic acid molecule, "Oligo C," that is not tethered to a bead, while graph 514 shows current measurements from Oligo C tethered to a bead. Graphs 508 and 512 generally show less time with non-zero current, when compared with counterpart graphs 510 and 514. In graph 510, for most of the time, current is non-zero, while in graph 508, current is zero or near zero for most of the time. Additionally, graph 510 shows a much more repetitive or periodic pattern of current fluctuations compared to graph 508. A current between the minimum and maximum current may indicate poor contact, a more resistive nucleotide, or the nucleotide in the process of forming or undoing contact with the electrodes, as these reasons may impact the quality of the tunneling effect.

Additional differences in current characteristics between tethered and non-tethered nucleic acid molecules can be seen in graphs 512 and 514. In graph 512, current is zero almost all of the time, with the exception of a few spikes in current. This pattern indicates that the nucleic acid molecule is not contacting the electrodes frequently. In contrast, graph 514 shows many spikes in current, occurring in a periodic or fairly periodic pattern. The pattern in graph 514 indicates that the nucleic acid molecule is contacting the electrodes frequently.

Graphs 508, 510, 512, and 514 show that nucleic acid molecules tethered to a bead provide stronger current signals than nucleic acid molecules that are allowed to flow freely through a channel. Signals may be clearer with tethered nucleic acid molecules and may allow for easier and more accurate identification of nucleotides.

II. Coplanar Electrodes in a Tunneling Break Junction

In some embodiments, tunneling recognition may be carried out between two electrodes that are substantially coplanar. The electrodes may be separated by a distance on the order of 2 nm, which may allow for tunneling recognition of a nucleotide. The electrodes may extend into an aperture, which has a diameter greater than 2 nm. The distance between the electrodes may then be independent of the aperture diameter.

In some embodiments, nanopore devices and methods may allow for a biological polymer molecule, not just nucleic acid molecules, to be analyzed. For example, a protein may be analyzed to determine the amino acids in the protein. The nanopore lengths and diameters may be adjusted for the size of an amino acid instead of the size of a nucleic acid molecule. For example, the distance between electrodes may be on the order of 1-2 nm. Nanopore devices and methods of tunneling recognition are discussed further below.

A. System

Figure 6A:
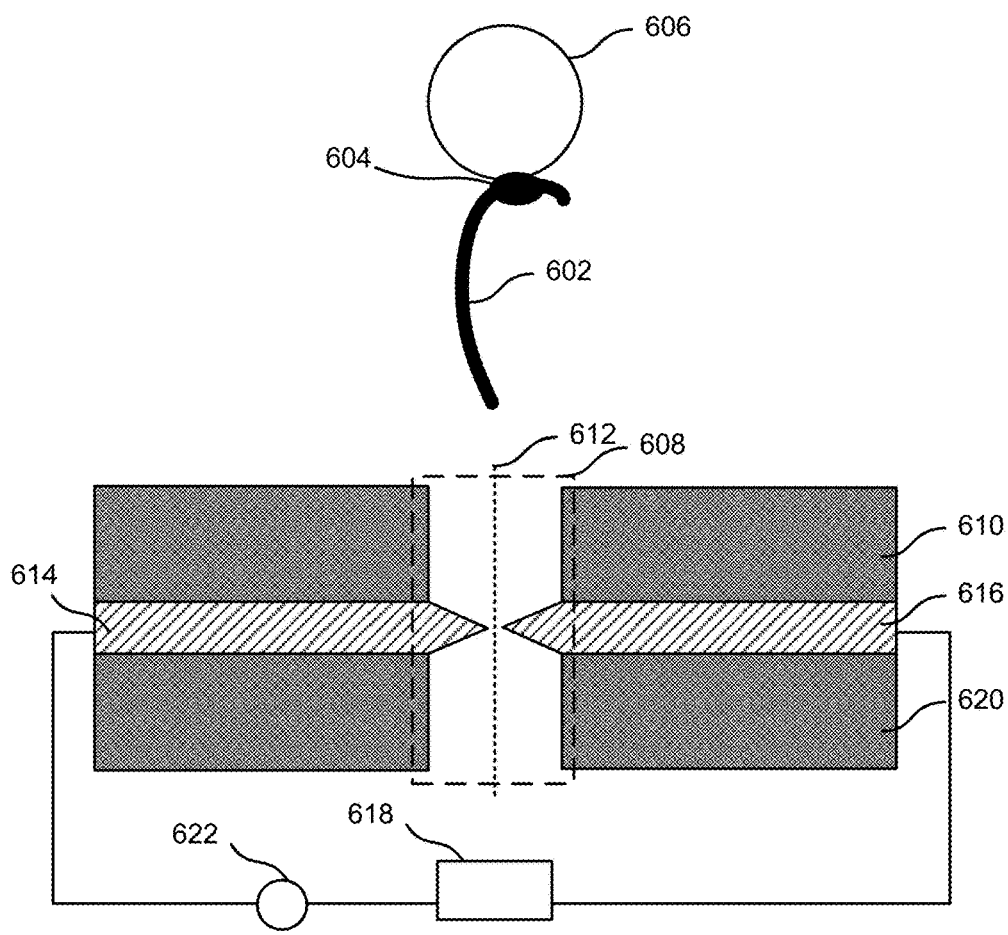
FIG. 6A shows a side cut view of a nucleic acid molecule analysis system 600 according to embodiments of the present invention.
Figure 6B:
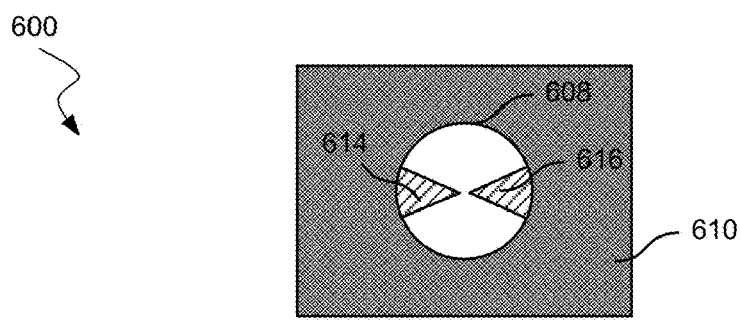
FIG. 6B shows a top view of a nucleic acid molecule analysis system 600 according to embodiments of the present invention.

As shown in FIG. 6A and FIG. 6B, embodiments may include a nucleic acid analysis system 600. FIG. 6A is a side cut view, and FIG. 6B is a top view. The top view may be on a surface of a silicon wafer or a microfluidic chip. System 600 may include a protein 604 attached to a particle 606 with a first diameter. Protein 604 may be any protein described herein, and particle 606 may be any particle described herein.

A nucleic acid molecule 602 may be introduced to the system with protein 104 already attached to particle 606. Nucleic acid molecule 602 may include any nucleic acid molecule described herein. Nucleic acid molecule 602 may attach to protein 604.

System 600 may also include an aperture 608 defined by a first insulator 610. The first insulator may include $Si_3N_4$, oxide insulators (e.g., $SiO_2$, $Al_2O_3$, oxide silicates), glass, quartz, or any insulator material described herein. Aperture 608 may have a second diameter smaller than the first diameter. The second diameter of aperture 608 may be larger than the diameter of the aperture 108 in FIG. 1A and 1B. The second diameter may be up to 50 nm. Aperture 608 may have a longitudinal axis 612 perpendicular to the diameter.

System 600 may further include a first electrode 614. A portion of first electrode 614 may extend into aperture 608. The first electrode may include gold, palladium, platinum, or any electrode material described herein.

System 600 may also include a second electrode 616, with a portion of second electrode 616 extending into the aperture. A plane that includes the portion of first electrode 614 and the portion of second electrode 616 may be orthogonal to the longitudinal axis. First electrode 614 and second electrode 616 may define a gap, which includes the shortest distance between the two electrodes. The shortest distance between first electrode 614 and second electrode 616 may be less than 1 nm, from 1 nm to 2 nm, from 2 nm to 3 nm, from 3 nm to 5 nm, from 5 nm to 10 nm, from 0.9 nm to 2.5 nm, from 0.9 nm to 1.0 nm, from 1.0 nm to 1.5 nm, from 1.5 nm to 2.0 nm, or from 2.0 nm to 2.5 nm in embodiments.

First electrode 614 and second electrode 616 may be formed by breaking a single nanowire into the two electrodes. Breaking may involve different techniques to separate a nanowire into two pieces that do not contact the other piece. Breaking the single nanowire may be by physically bending a semiconductor chip with the nanowire on it. Bending the chip may then break the wire and may create a gap between the two parts of the broken nanowire. The second diameter of aperture 608 may be large enough to accommodate the mechanical bending of the chip. The electrode may also be broken by being cut with a beam or by applying a high electrical potential. The second electrode may be any electrode material described herein.

FIGS. 6A and 6B show first electrode 614 and second electrode 616 having a triangular or conical shape in the aperture. The shape of the electrodes may be formed by repeated back-and-forth bending of the chip until the electrodes touch. An applied electrical potential then may help shape the tips of the electrodes. In other embodiments, the portion of first electrode 614 closest to second electrode 616 may not come to a point. Instead, the ends of the electrodes may be flat or hemispherical.

In addition, system 600 may include a first power supply 618 in electrical communication with first electrode 614 and the second electrode 616. First power supply 618 may be apply a voltage to first electrode 614 and second electrode 616. First power supply 618 may be configured to maintain a desired current or a desired voltage. Current passing through the electrodes may be measured by a meter device 622. Meter device 622 may be configured to measure current through the electrodes along and through a portion of the nucleic acid molecule bridging the electrodes. Meter device 622 may be any meter device described herein.

First electrode 614 may be between first insulator 610 and a second insulator 620. Similarly, second electrode 616 may be between first insulator 610 and second insulator 620. First insulator 610 and second insulator 620 may include silicon nitride, silicon dioxide, glass, quartz, and other insulating materials described herein. Photoresist may be difficult to shape on the scale needed for the first insulator in a tunneling break junction. The insulator material may extend farther than what is shown in FIGS. 6A and 6B, for the insulator material may be the majority material of a microfluidic chip.

In some embodiments, system 600 may include a second power supply (not shown). The second power supply may be configured to apply an electric field that would move a nucleic acid molecule through aperture 608. The electric field may be applied across the layers that make up the aperture. As with system 100 in FIG. 1, system 600 may have a liquid disposed in aperture 608. The power supply may be in electrical communication with a third electrode and a fourth electrode. The third electrode and fourth electrode may be disposed in a liquid and disposed on opposite ends of aperture 608.

First insulator 610 and second insulator 620 may be attached to a microfluidic chip, including a silicon chip. The insulators may be deposited or formed on top of a semiconductor material or may be patterned from the semiconductor material. The semiconductor material may include a silicon wafer.

Systems may also include a biological polymer analysis system, where a biological polymer molecule, instead of a nucleic acid molecule, is analyzed. For example, a system similar to system 600 may be used to analyze a protein and the amino acids of the protein.

B. Method

Figure 7:
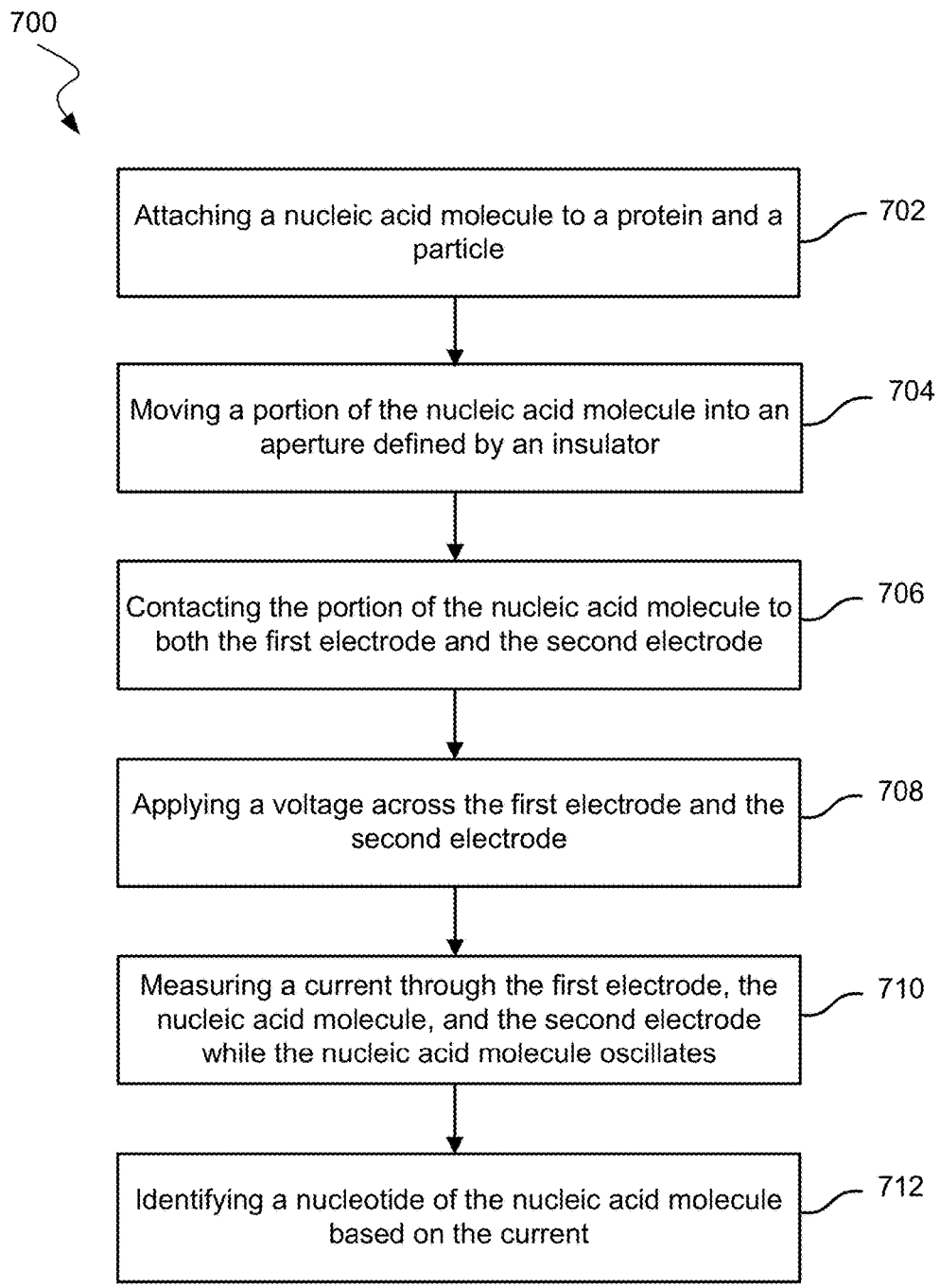
FIG. 7 shows a flowchart a method 700 of analyzing a nucleic acid molecule according to embodiments of the present invention.

As shown in FIG. 7, additional embodiments may include a method 700 of analyzing a nucleic acid molecule.

At block 702, method 700 may include attaching a nucleic acid molecule to a protein. The protein may be attached to a particle with a first diameter.

At block 704, method 700 may also include moving a portion of the nucleic acid molecule into an aperture defined by an insulator. The portion of the nucleic acid molecule may include a nucleotide. The aperture may have a second diameter less than the first diameter.

Moving the portion of the nucleic acid molecule may include applying an electric field to drive the nucleic acid molecule through the aperture. In these and other embodiments, moving the portion may include moving the nucleic acid molecule with a pressure-driven liquid flow. A convective liquid flow may be used to push the nucleic acid molecule through the aperture. A flowing liquid to move nucleic acid molecules may be more effective with a system similar to system 600 in FIG. 6A and 6B compared to system 100 in FIG. 1A and 1B. System 100 may be only about 10 to 20 nm thick, and a liquid flow may break the sandwich of various layers. On the other hand, system 600 may be fabricated to be thicker than system 100. Additionally, parts of system 600, including the insulator, may be strongly attached to a wafer or other material, which may provide greater stability in a flowing liquid.

Method 700 may further include moving the portion of the nucleic acid molecule into a gap between a first electrode and a second electrode. The gap may include a line representing the shortest distance between the electrodes. Moving the portion of the nucleic acid molecule may include using the same forces that moved the portion into the aperture.

At block 706, method 700 may include contacting the portion of the nucleic acid molecule to both the first electrode and the second electrode. The portion of the nucleic acid molecule may contact the first electrode and the second electrode within the aperture.

Figure 8A:
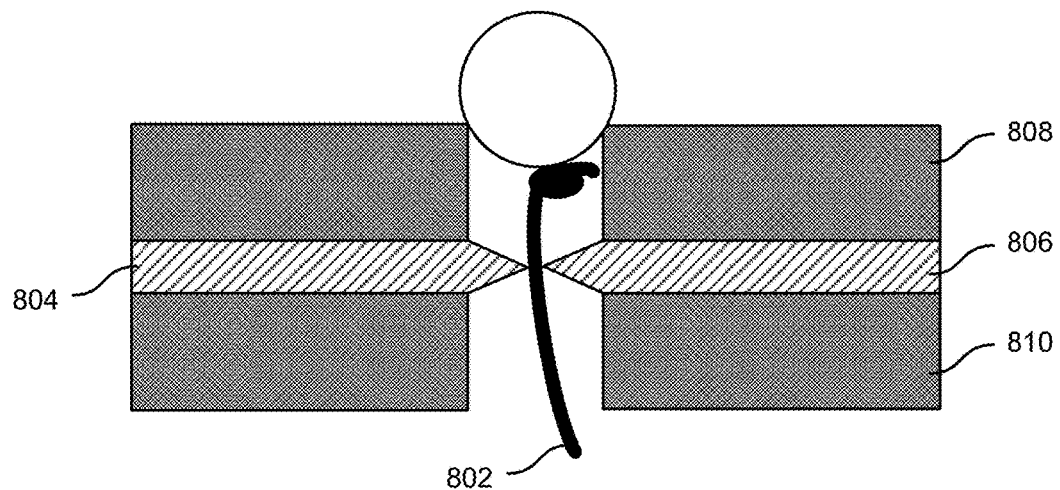
FIG. 8A shows a nucleic acid molecule contacting two electrodes in a nucleic acid molecule analysis system according to embodiments of the present invention.
Figure 8B:
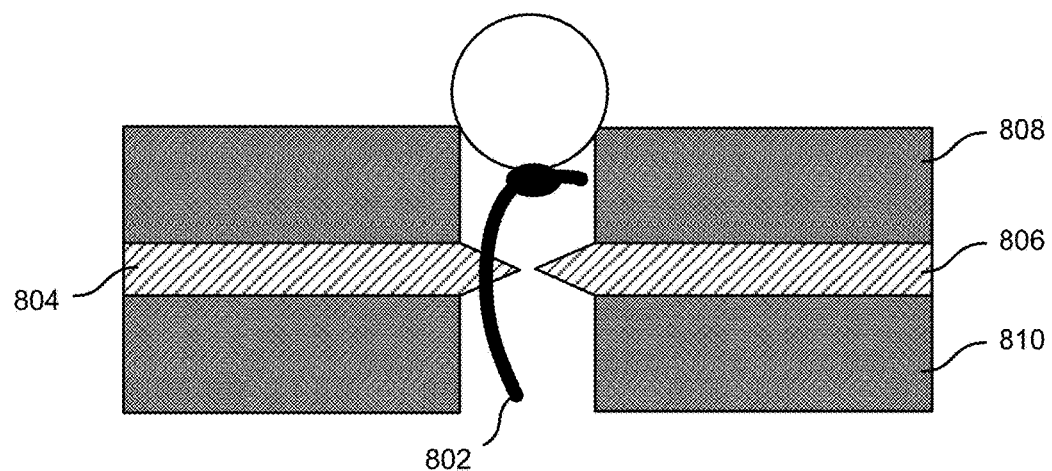
FIG. 8B shows a nucleic acid molecule not contacting two electrodes in a nucleic acid molecule analysis system according to embodiments of the present invention.

FIG. 8A shows a nucleic acid molecule 802 contacting first electrode 804 and second electrode 806, with both electrodes electrically isolated in insulators 808 and 810. When nucleic acid molecule 802 contacts both electrodes, the molecule may also be considered to bridge both electrodes. During this contact, electrons may tunnel from one electrode to the other. The current generated by the tunneling electrodes may be measured. As shown in FIG. 8B, if nucleic acid molecule does not contact first electrode 804 or second electrode 806, then no electrons may tunnel through the electrodes and no current may be measured. As shown in FIG. 8B, nucleic acid molecule 802 may contact only first electrode 804 and not second electrode 806.

At block 708, method 700 may include applying a voltage across the first electrode and the second electrode. The electrodes may be considered tunneling electrodes and may be any electrode described herein. The voltage may be direct current or alternating current voltage. The voltage may be applied in pulses or in a waveform (e.g., sine, square, triangle, or sawtooth). Method 700 may also include applying a current through the first electrode and the second electrode At block 710, a current through the first electrode, the nucleic acid molecule, and the second electrode may be measured while the nucleic acid molecule oscillates in the aperture.

At block 712, based on the current, the nucleotide of the portion of the nucleic acid molecule may be identified, similar to methods described herein.

In other embodiments, methods may be used to analyze a biological polymer other than a nucleic acid molecule. For example, the amino acids, rather than the nucleotides, of a protein, rather than a nucleic acid molecule, may be analyzed by methods similar to method 700.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A method of analyzing a nucleic acid molecule, the method comprising:
   attaching the nucleic acid molecule to a protein and a particle having a first diameter;
   moving a portion of the nucleic acid molecule into an aperture defined by a first insulator, the aperture having a second diameter less than the first diameter, and the portion comprising a nucleotide;
   applying a voltage across a first electrode and a second electrode;
   contacting the portion of the nucleic acid molecule to both the first electrode and the second electrode within the aperture;
   measuring a current through the first electrode, the portion of the nucleic acid molecule, and the second electrode; and
   identifying the nucleotide of the portion of the nucleic acid molecule based on the current.

2. The method of claim 1, wherein the protein is a molecular motor protein selected from the group consisting of polymerases, helicases, ribosomes, and exonucleases.

3. The method of claim 1, wherein the nucleic acid molecule comprises single-stranded DNA, RNA, or circular DNA.

4. The method of claim 1, further comprising:
   measuring an amplitude and a frequency of the current while the nucleic acid molecule oscillates in the aperture.

5. The method of claim 1, further comprising:
   measuring a pulse width of the current while the nucleic acid molecule oscillates in the aperture.

6. The method of claim 1, further comprising comparing the current to a calibration current measured from a known nucleotide.

7. The method of claim 1, wherein the nucleotide comprises a nucleotide labeled with a chemical compound that yields an increased tunneling current relative to an unlabeled nucleotide.

8. The method of claim 1, further comprising moving the portion of the nucleic acid molecule into a gap between the first electrode and the second electrode, the gap comprising a line representing the shortest distance between the first electrode and the second electrode.

9. The method of claim 8, wherein the shortest distance between the first electrode and the second electrode is 2 nm or less.

10. The method of claim 1, wherein moving the portion of the nucleic acid molecule into the aperture comprises moving the portion of the nucleic acid molecule with an applied electric field or a pressure-driven flow.

11. The method of claim 1, wherein:
    the aperture has a longitudinal axis perpendicular to the second diameter,
    a portion of the first electrode extends into the aperture,
    a portion of the second electrode extends into the aperture,
    a plane comprising the portion of the first electrode and the portion of the second electrode is orthogonal to the longitudinal axis.

12. The method of claim 1, wherein:
    the aperture is defined by a sidewall,
    the sidewall comprises a second insulator, the first electrode, the first insulator, the second electrode, and a third insulator,
    the second insulator is in contact with the first electrode,
    the first electrode is in contact with the first insulator,
    the first insulator is in contact with the second electrode, and
    the second electrode is in contact with the third insulator.

13. The method of claim 1, wherein:
    moving the portion of the nucleic acid molecule into the aperture comprises applying an electric field, and
    the aperture is further defined by a first electrode and a second electrode.

14. The method of claim 13, wherein the second diameter is in a range from 10 nm to 15 nm.

15. The method of claim 13, wherein the first diameter is 10 nm or more.

16. The method of claim 13, wherein the first insulator has a thickness of 2 nm or less.

17. The method of claim 13, wherein the portion of the nucleic acid molecule is a first portion of the nucleic acid molecule, the method further comprising:
    moving, using the protein, the nucleic acid molecule such that a second portion of the nucleic acid molecule contacts both the first electrode and the second electrode, wherein:
       the second portion of the nucleic acid molecule is at a different location than the first portion of the nucleic acid molecule, and
       the second portion of the nucleic acid molecule comprises a second nucleotide.

18. A nucleic acid molecule analysis system, the system comprising:
    a protein attached to a particle, the particle having a first diameter;
    an aperture defined by a first electrode, a first insulator, and a second electrode, the aperture having a second diameter less than the first diameter;
    a first power supply in electrical communication with the first electrode and the second electrode;
    a second power supply configured to apply an electric field through the aperture to move the protein attached to the particle to the aperture; and
    a meter device configured to measure a current through the first electrode and the second electrode when a first portion of a nucleic acid molecule attached to the protein contacts the first electrode and the second electrode.

19. The system of claim 18, wherein the system further comprises the nucleic acid molecule attached to the protein.

20. The system of claim 18, wherein the first insulator comprises a photoresist.

21. The system of claim 18, wherein:
the aperture is further defined by a sidewall, and
the sidewall comprises a second insulator, the first electrode, the first insulator, the second electrode, and a third insulator.

22. The system of claim 21, wherein:
the first electrode is disposed between the second insulator and the first insulator, and
the second electrode is disposed between the first insulator and the third insulator.

23. The system of claim 19, wherein at least one of the first electrode and the second electrode is coated with an adapter molecule, wherein the adapter molecule undergoes weak force chemical interactions with the nucleic acid molecule.

24. A nucleic acid analysis system, the system comprising:
a protein attached to a particle, the particle having a first diameter;
an aperture defined by a first insulator, the aperture having a second diameter smaller than the first diameter, and the aperture having a longitudinal axis perpendicular to the second diameter;
a first electrode, wherein a portion of the first electrode extends into the aperture;
a second electrode, wherein a portion of the second electrode extends into the aperture and wherein a plane comprising the portion of the first electrode and the portion of the second electrode is orthogonal to the longitudinal axis;
a first power supply in electrical communication with the first electrode and the second electrode; and
a meter device configured to measure a current through the first electrode and the second electrode when a first portion of a nucleic acid molecule attached to the protein contacts the first electrode and the second electrode.

25. The system of claim 24, further comprising the nucleic acid molecule attached to the protein.

26. The system of claim 24, further comprising a second power supply configured to apply an electric field through the aperture.

27. The system of claim 24, wherein the first electrode is disposed between the first insulator and a second insulator.

28. The system of claim 24, wherein the second electrode is disposed between the first insulator and a second insulator.

29. The system of claim 24, wherein:
the first electrode and the second electrode define a gap,
the gap comprises the shortest distance between the first electrode and the second electrode, and
the shortest distance between the first electrode and the second electrode is 2 nm or less.

30. The system of claim 29, wherein the system is attached to a microfluidic silicon chip.

* * * * *